United States Patent [19]

Maender et al.

[11] Patent Number: 4,614,817

[45] Date of Patent: Sep. 30, 1986

[54] MAKING NITRODIARYLAMINES

[75] Inventors: Otto W. Maender, Copley; Helmut L. Merten, Hudson, both of Ohio

[73] Assignee: Monsanto Company, St. Louis, Mo.

[21] Appl. No.: 562,767

[22] Filed: Dec. 19, 1983

[51] Int. Cl.$^4$ .............................................. C07C 85/04
[52] U.S. Cl. .................................... 564/406; 564/414
[58] Field of Search ............................... 564/406, 414

[56] References Cited

U.S. PATENT DOCUMENTS

| | | | |
|---|---|---|---|
| 3,053,896 | 9/1962 | Luvisi et al. | 564/406 |
| 3,435,074 | 3/1969 | Terao et al. | 564/406 |
| 4,140,716 | 2/1979 | Maender et al. | 564/132 |
| 4,187,248 | 2/1980 | Merten et al. | 564/414 |
| 4,187,249 | 2/1980 | Maender et al. | 564/414 |
| 4,196,146 | 4/1980 | Merten et al. | 564/414 |
| 4,209,463 | 6/1980 | Maender et al. | 564/414 |
| 4,228,103 | 10/1980 | Wright | 564/414 |

OTHER PUBLICATIONS

J. Org. Chem., vol. 42, No. 10, 1977, Synthesis of 4-Aminodiphenylamine and Its Relatives, C. S. Rondestvedt, Jr.

Primary Examiner—Robert V. Hines
Attorney, Agent, or Firm—Gordon B. Seward

[57] ABSTRACT

Nitrodiarylamines, useful as intermediates, are produced by combining a formyl derivative of an aromatic primary amine with a nitrohaloarene, at condensation temperature for forming nitrodiarylamine, and adding an alkoxide or cycloalkoxide of an alkali metal, excluding lithium.

19 Claims, No Drawings

MAKING NITRODIARYLAMINES

BACKGROUND OF THE INVENTION

This invention relates to a method for making nitrodiarylamines, useful as intermediates for preparing dyestuffs and antidegradants. For example, 4-nitrodiphenylamine is used as an intermediate in preparing antiozonants useful in rubber compounds.

It is known to make nitrodiarylamines from nitrohaloarenes and N-acylaromatic amines or other activated forms of the amines in the presence of a so-called acid acceptor, for example, sodium carbonate. This process suffers from disadvantages, since it requires large amounts of the "acid acceptor" and large amounts of by-products are formed.

An improved process is shown in U.S. Pat. No. 4,187,248, in which process a nitrohaloarene, such as p-nitrochlorobenzene is reacted with a sodium, potassium, rubidium or cesium salt of the formyl derivative of an aromatic primary amine, such as potassium formanilide. The process is a batch reaction, and is exothermic, and since all of the reactants are present in the reactor from the outset, temperature and the rate of reaction are difficult to control.

SUMMARY OF THE INVENTION

The instant invention provides an improved process for producing nitrodiarylamines. Briefly, the process involves combining the formyl derivative of an aromatic primary amine with a nitrohaloarene at condensation temperature for forming nitrodiarylamine and adding an alkoxide or cycloalkoxide of sodium, potassium, rubidium or cesium. Lithium alkoxides are insufficiently reactive.

The exact mechanism of the reaction is not known, but it is thought that the alkoxide or cycloalkoxide immediately reacts with the formyl derivative of the aromatic primary amine to form the corresponding salt of the latter in situ, which salt then reacts rather rapidly with the nitrohaloarene to produce the nitrodiarylamine. In the formation of the salt, the alcohol corresponding to the alkoxide is also formed and is either removed from the reaction zone or allowed to remain as an inert diluent. It can be seen that control of the rate of alkoxide addition serves to control the rate of the overall reaction, thus avoiding the possiblity of excessive and dangerous temperature buildup in the reaction zone and unwanted side reactions which can occur at higher temperatures.

DETAILED DESCRIPTION

The process of the invention is believed to be a general one for condensation of formyl derivatives of aromatic primary amines, but has been examined most extensively with formanilides, and especially with formanilide itself. Formanilides substituted in the benzene nucleus by one or more substituents inert under the reaction conditions, for example, one or more alkyl, alkoxy, nitro, fluoro or chloro substituents are suitable. Illustrative substituted formanilides which may be used in the process are 3-chloroformanilide, 4-chloroformanilide, 2-methylformanilide, 3-methylformanilide, 3-ethylformanilide, 3,4-dimethylformanilide, 3-methoxyformanilide, 4-methoxyformanilide, 4-ethylformanilide, 4-isopropylformanilide, 4-butylformanilide 3,4-dichloroformanilide and 4-nitroformanilide.

A variety of nitrohaloarenes have been proposed for making nitrodiarylamines, any of which appear to be suitable for use in the process of the invention. Illustrative of such nitrohaloarenes are: o-nitrochlorobenzene, o-nitrobromobenzene, p-nitrochlorobenzene, p-nitrobromobenzene, m-nitrochlorobenzene, m-nitrobromobenzene, 1-chloro-2-methyl-4-nitrobenzene, 1-chloro-3-methyl-4-nitrobenzene 1-chloro-2-nitronaphthalene, 3,4-dichloronitrobenzene, 3-methyl-4-chloronitrobenzene, 2-methyl-4-chloronitrobenzene, 2-ethyl-4-chloronitrobenzene, 2,3-dimethyl-4-chloronitrobenzene, 2,5-dimethyl-4-chloro-nitrobenzene, 3,5-dimethyl-4-chloronitrobenzene and p-nitrofluorobenzene.

Generally, it is preferred to use a molar ratio of about 1.0 to 2.0 moles of the formyl derivative of the aromatic primary amine per mole of nitrohaloarene, and more preferably 1.2 to 1.8 moles.

Preferred alkoxides of sodium, potassium, rubidium and cesium are those which can be formed by replacement of the hydroxyl hydrogen atom of alkyl alcohols of from 1–12 carbon atoms or cycloalkyl alcohols of from 4–12 carbon atoms. The alkoxides can be also be alkyl-substitited cycloalkyl, as, for example, 2-methylcyclohexyl, 4-ethylcyclooctyl and the like alkoxides. Alkoxides from hindered alcohols are among those preferred, such as, for example, potassium tertiary butoxide, sodium tertiary amyloxide, cesium-4-methylpentan-2-oxide and the like. The amount of alkoxide added should be about equimolar with the formyl derivative of the aromatic primary amine charged, but more (up to about a 50% molar excess) or less (to a 20% molar deficiency) can be used.

The alkoxides can be added neat to the reaction zone, but since they are solids at ordinary temperatures it is easier and more convenient to add them in solution in an appropriate solvent. Any non-reactive solvent in which the alkoxides are soluble can be used, but it is preferred to use alcohols, especially alkyl or cycloalkyl alcohols. The alkoxides are most conveniently made by replacing the hydroxyl hydrogen of an alkyl or cycloalkyl alcohol with an atom of the alkali metal (excluding lithium). In the case of some alcohols, such as straight-chain alcohols, the alcohol is reacted with an alkali metal hydroxide (again excluding lithium). Alkoxides of hindered alcohols are not so easy to prepare, and may be made by reacting the alcohol with metallic sodium, potassium, rubidium or cesium. In any case, since the alkoxide is usually made from the alcohol, it is most convenient to employ an excess of alcohol, thus producing the alkoxide in solution in the alcohol from which it was made. It is not necessary, however, that the solvent alcohol be the same as that from which the alkoxide is derived.

As has been explained, the alkoxide is added to the reaction zone, and this addition can be a continuous or an intermittent addition. The rate of addition of the alkoxide will determine the rate of the reaction. The alkoxide is consumed rapidly and the reaction produces the corresponding alcohol, which can be left in the reaction zone to act as a solvent for reactants and product or removed from the reaction zone. If the alcohol is relatively volatile, it can be easily removed from the reaction zone by removing vapors, condensing the vapors and then separating the alcohol therefrom. The lower boiling alcohols show a tendency to promote increased nucleophilic attack on nitrohaloarenes. However, since the lower boiling alcohols can be easily removed from the reaction zone, this tendency can be minimized. The hindered alcohols are less likely to promote such an attack when they are used, even if they are allowed to remain in the reaction zone as diluents.

The process of the invention is operable at any temperature at which condensation occurs to form the nitrodiarylamine product. This temperature will be determined by the reactivity of the particular reactants chosen, and can also be determined by the speed at which the reaction can be practically performed, among other factors. Preferred reaction temperatures will range from about 100° up to about 230° C., and more preferably between 130° and 180° C.

Although it is not essential, it is preferred that the process of the invention be performed under agitation, in order to maximize the contact of the reactants with each other and to improve temperature control.

The reaction may be carried out in mild steel, stainless steel, glass or glass-lined vessels. After the condensation reaches the selected end-point, the alkali metal halide byproduct may be removed by water washing, the solvent, if present, removed by distillation, and the residue cooled to about 5° C. to recover nitrodiarylamine by crystallization.

EXAMPLE 1

Potassium 2-methyl-2-butoxide was first prepared by the following method:

Metallic potassium, 19.6 grams, was dissolved in 467 grams of t-amyl alcohol (2-methyl-2-butanol). The alcohol was charged to a vessel and heated to 60°–65° C. under a nitrogen head. The potassium was added to the vessel in small chunks, and was observed to melt at about 60°. A heating mantle maintained the desired temperature in the vessel for a six-hour period.

The clear product was decanted hot under nitrogen and allowed to cool. This material, a straw-colored liquid, was calculated as 13.4% potassium 2-methyl-2-butoxide in t-amyl alcohol.

The alkoxide prepared above was then used in the preparation of 4-nitrodiphenylamine according to the following reaction:

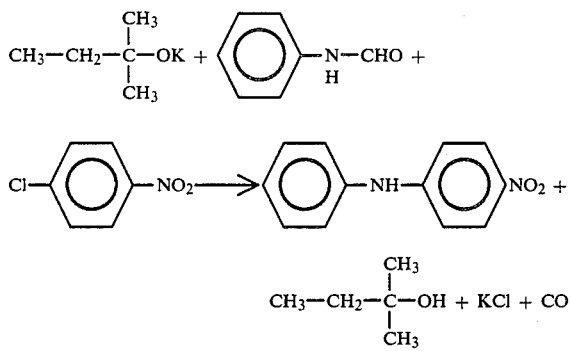

The procedure was as follows:

To a 500 ml, three-neck round-bottom flask with thermometer well (fitted with a two-plate packed column, distillation head and 500 ml dropping funnel with side arm) was added 47.3 g (0.3 mole) p-nitrochlorobenzene and 105.4 g (0.87 mole) formanilide. To this stirring melt at 155°–160° C. was added, dropwise, a solution of 310.9 g (0.33 mole) 13.4% potassium 2-methyl-2-butoxide (prepared above) over a 200 minute period. The condensed distillate was collected, accumulating 356 ml, and the pot was held at temperature for an additional 35 minutes after all the alkoxide solution had been added, at which time a total of 9.0 liters of CO had also been collected.

The reaction mass was then vacuum stripped, quenched with 200 ml xylene and washed with 200 ml 90° C. water. Together with 50 ml xylene used to wash the reaction flask, the materials were added to a separatory funnel and washed again with 200 ml of 90° C. The xylene layer was then transferred to a beaker and cooled to 5° C. The resultant bright orange crystals, weighing 41.8 g (0.1951 mole 4-nitrodiphenylamine) were filtered off. The mother liquor filtrate (310.5 g) was analyzed as containing aniline (0.0617 mole), p-nitrochlorobenzene (0.0052 mole), formanilide (0.4448 mole), diphenyl formamide (0.0065 mole), 4-nitrodiphenylamine (0.0852 mole), triphenylamine (0.0014 mole) and 2-nitrodiphenylamine (0.0014 mole). No azo compounds were observed.

The distillate (294.4 g) was principally t-amyl alcohol, but contained aniline (0.0021 mole), p-nitrochlorobenzene (0.0012 mole) and formanilide (0.0013 mole).

Overall, conversion was calculated (based on p-nitrochlorobenzene) at 97.9%, and the yield of 4-nitrodiphenylamine at 93.4%.

EXAMPLE 2

In a manner similar to that of Example 1, potassium 4-methylpentan-2-oxide was used as the alkoxide in preparing 4-nitrodiphenylamine, except that 0.49 mole of formanilide was charged instead of 0.87 mole. The reaction vessel temperature was 147°–150° C., the feed time 120 minutes and the total time 210 minutes. Conversion was 90% and yield, 73.2%. Both figures reflect the lower amount of excess formanilide, however, the amount of byproducts was less than in Example 1.

EXAMPLES 3–10

In a manner similar to the preceding examples a series of reactions was run using different alkoxides in solution in their respective alcohols. In all of the reactions, 0.3 mole of p-nitrochlorobenzene, 0.49 mole of formanilide and 0.3 mole of the alkoxide were used. Reaction temperatures were controlled at 175° C., and the reactions were continued for 15 minutes after the alkoxide addition was complete. The conditions and results are set forth in Table I.

In Examples 3 and 4 the alkoxide solution was added below the surface of the reactants, by means of a peristaltic pump. A comparison of Examples 4 and 5 indicates that better results could be expected using the pump.

EXAMPLES 11–17

Another series of alkoxides was run in the same manner as Examples 5–10, above. Conditions and results are set forth in Table II.

TABLE I

| Example | Alkoxide | Total Reaction Time, min. | % Yield | % Conversion |
|---|---|---|---|---|
| 3 | K 2-butoxide | 126 | 81.3 | 91.6 |
| 4 | K 2-methyl-2-butoxide | 144 | 83.6 | 93.4 |
| 5 | K 2-methyl-2-butoxide | 300 | 74.2 | 88.5 |
| 6 | Na 2-methyl-2-butoxide | 405 | 67.7 | 80.0 |
| 7 | K isopropoxide | 132 | 86.4 | 94.1 |
| 8 | K 2-octyloxide | 105 | 54.0 | 81.7 |
| 9 | K t-butoxide | 252 | 87.1 | 95.9 |
| 10 | K n-butoxide | 126 | 70.7 | 86.0 |

TABLE II

| Example | Alkoxide | Total Reaction Time, min. | % Yield | % Conversion |
|---|---|---|---|---|
| 11 | Na methoxide | 204 | 48.6 | 85.8 |
| 12 | K methoxide | 174 | 70.9 | 86.1 |
| 13 | K 2-pentanoxide | 135 | 85.0 | 90.5 |
| 14 | K 3-methyl-1-butoxide | 144 | 65.3 | 86.7 |
| 15 | K 1-pentanoxide | 165 | 57.8 | 86.2 |
| 16 | Cs 2-methyl-2-butoxide | 120 | 80.1 | 88.4 |
| 17 | Rb 2-methyl-2-butoxide | 138 | 85.5 | 96.0 |

TABLE III

| Example | Nitrohaloarene | Formanilide | Alkoxide | Reaction °Temp. | Total Reaction Time, min. | % Yield | % Conversion |
|---|---|---|---|---|---|---|---|
| 18 | PNCB | FAN | NaMIBC/KMIBC, 6/1 | 175 | 180 | 71.8 | 86.8 |
| 19 | PNCB | FAN | NaMIBC + 10% KCl | 175 | 216 | 63.0 | 84.6 |
| 20 | PNFB | FAN | KMIBC | 165 | 192 | 81.8 | 96.9 |
| 21 | PNFB | FAN | KIP | 165 | 120 | 88.2 | 99.5 |
| 22 | PNCB | 4-MeFAN | KIP | 175 | 120 | 82.9 | 93.1 |
| 23 | PNCB | 4-ClFAN | KIP | 165 | 138 | 86.1 | 87.8 |
| 24 | PNCB | 4-NFAN | K2B | 175 | 270 | 65.5 | 83.5 |
| 25 | ONCB | FAN | KMIBC | 175 | 105 | 68.9 | 76.0 |

In Example 16 the temperature was controlled at 145° C., in Example 17, at 160° C.

EXAMPLES 18-25

Further variations of the reactions were performed using a variety of reactants. In each reaction 0.3 mole of nitrohaloarene and 0.49 mole of a formanilide were reacted, with 0.33 mole of an aloxide (in solution in its alcohol) added dropwise. Conditions and results of the reactions are set forth in Table III. The abbreviations used are as follows:

| ABBREVIATION | COMPOUND |
|---|---|
| PNCB | p-nitrochlorobenzene |
| PNFB | p-nitrofluorobenzene |
| ONCB | o-nitrochlorobenzene |
| FAN | formanilide |
| 4-MeFAN | 4-methylformanilide |
| 4-ClFAN | 4-chloroformanilide |
| 4-NFAN | 4-nitroformanilide |
| NaMIBC | sodium 2-methyl-2-butoxide |
| KMIBC | potassium 2-methyl-2-butoxide |
| KCl | potassium chloride |
| KIP | potassium isopropoxide |
| K2B | potassium 2-butoxide |

Note: MIBC is derived from "methyl isobutylcarbinol", a common name for 2-methyl-2-butanol.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. The method of producing a nitrodiarylamine comprising the steps of
    (A) combining the formyl derivative of an aromatic primary amine and a nitrohaloarene at condensation temperature for forming nitrodiarylamine and
    (B) admixing thereto a sodium, potassium, rubidium or cesium alkoxide.

2. The method of claim 1 wherein the alkoxide is in solution in an alkyl or cycloalkyl alcohol.

3. The method of claim 1 wherein the alkoxide is added continuously.

4. The method of claim 1 wherein the alkoxide is added intermittently.

5. The method of claim 1 wherein the alkoxide is a sodium alkoxide, a potassium alkoxide or a combination thereof.

6. The method of producing a nitrodiarylamine comprising the steps of
    combining in a reaction zone a monohalonitrobenzene and at least a molar equivalent of a formanilide, maintaining the contents of the reaction zone at a temperature of from 100° C. to 230° C. under agitation and adding to the reaction zone a solution of a compound of the formula ROM in an alcohol of the formula R'OH, wherein M is sodium, potassium, rubidium or cesium and R and R' are the same or different alkyl radicals of 1 to 12 carbon atoms or cycloalkyl radicals of 4 to 12 carbon atoms.

7. The method of claim 6 wherein the contents of the reaction zone are maintained at a temperature of from 130° C. to 180° C.

8. The method of claim 6 wherein R and R' are the same.

9. The method of claim 8 wherein R and R' are both secondary or tertiary alkyl.

10. The method of claim 6 wherein M is sodium or potassium or a mixture thereof.

11. The method of claim 6 wherein M is sodium and a minor amount of potassium salt is present.

12. The method of producing 4-nitrodiphenylamine comprising the steps of
    (A) combining in a reaction zone paranitrochlorobenzene and a molar excess of formanilide at condensation temperature for forming 4-nitrodiphenylamine and
    (B) gradually charging to the reaction zone a solution of a compound of the formula ROM in an alcohol of the formula R'OH wherein R and R' are the same alkyl radicals of from 4 to 8 carbon atoms and M is sodium, potassium, rubidium or cesium.

13. The method of claim 12 wherein M is potassium.

14. The method of claim 12 wherein R and R' are 4-methyl-2-pentyl.

15. The method of claim 12 wherein R and R' are tertiary butyl.

16. The method of claim 12 wherein the contents of the reaction zone are maintained at a temperature of from 130° C. to 180° C.

17. The method of claim 12 wherein the solution is charged at a rate so as to control the temperature of the reaction zone between 100° C. and 230° C.

18. The method of claim 12 wherein about 1.67 moles formanilide are charged to the reaction zone per mole of paranitrochlorobenzene.

19. The method of claim 12 wherein a diluent of the formula R'OH is combined with the formanilide and paranitrochlorobenzene in the reaction zone.

* * * * *